(12) United States Patent
Benson et al.

(10) Patent No.: US 10,874,362 B2
(45) Date of Patent: Dec. 29, 2020

(54) SYSTEMS AND METHODS FOR DIGITAL X-RAY IMAGING

(71) Applicant: Illinois Tool Works Inc., Glenview, IL (US)

(72) Inventors: Paul Benson, Waltham, MA (US); Brian Girouard, Billerica, MA (US); Amine Belarbi, Whitman, MA (US)

(73) Assignee: Illinois Tool Works Inc., Glenview, IL (US)

( * ) Notice: Subject to any disclaimer, the term of this patent is extended or adjusted under 35 U.S.C. 154(b) by 0 days.

(21) Appl. No.: 16/269,459

(22) Filed: Feb. 6, 2019

(65) Prior Publication Data

US 2019/0239834 A1 Aug. 8, 2019

Related U.S. Application Data

(60) Provisional application No. 62/627,469, filed on Feb. 7, 2018, provisional application No. 62/627,473, filed
(Continued)

(51) Int. Cl.
*A61B 6/00* (2006.01)
*G01T 1/20* (2006.01)
(Continued)

(52) U.S. Cl.
CPC .............. *A61B 6/4405* (2013.01); *A61B 6/06* (2013.01); *A61B 6/107* (2013.01); *A61B 6/405* (2013.01);
(Continued)

(58) Field of Classification Search
USPC ....................................................... 378/102
See application file for complete search history.

(56) References Cited

U.S. PATENT DOCUMENTS

| 4,856,036 A | 8/1989 | Malcolm |
| 5,784,434 A | 7/1998 | Shieh |

(Continued)

FOREIGN PATENT DOCUMENTS

| JP | 2003279500 | 10/2003 |
| WO | 2005081956 A2 | 9/2005 |

(Continued)

OTHER PUBLICATIONS

CMOS X-Ray Detectors for Industrial Non-Destructive Testing, Teledyne DALSA Industrial X-Ray Detectors X-Ray Solutions for Non-Destructive Testing, Teledyne Dalsa.

(Continued)

*Primary Examiner* — Hoon K Song
(74) *Attorney, Agent, or Firm* — McAndrews, Held & Malloy, Ltd.

(57) ABSTRACT

Systems and methods for digital X-ray imaging are disclosed. An example portable X-ray scanner includes: an X-ray detector configured to generate digital images based on incident X-ray radiation; an X-ray tube configured to output X-ray radiation; a computing device configured to control the X-ray tube, receive the digital images from the X-ray detector, and output the digital images to a display device; a power supply configured to provide power to the X-ray tube, the X-ray detector, and the computing device; and a frame configured to: hold the X-ray detector, the computing device, and the power supply; and hold the X-ray tube such that the X-ray tube directs the X-ray radiation to the X-ray detector.

18 Claims, 12 Drawing Sheets

Related U.S. Application Data on Feb. 7, 2018, provisional application No. 62/627,464, filed on Feb. 7, 2018, provisional application No. 62/627,466, filed on Feb. 7, 2018.

(51) Int. Cl.

| | | |
|---|---|---|
| *H01J 35/02* | (2006.01) | |
| *G01T 7/00* | (2006.01) | |
| *A61B 6/06* | (2006.01) | |
| *G01T 1/24* | (2006.01) | |
| *H04N 5/321* | (2006.01) | |
| *A61B 6/10* | (2006.01) | |
| *G21F 1/08* | (2006.01) | |

(52) U.S. Cl.
CPC ............ *A61B 6/4441* (2013.01); *A61B 6/467* (2013.01); *A61B 6/487* (2013.01); *A61B 6/54* (2013.01); *A61B 6/56* (2013.01); *G01T 1/20* (2013.01); *G01T 1/2002* (2013.01); *G01T 1/2018* (2013.01); *G01T 1/24* (2013.01); *G01T 7/00* (2013.01); *G21F 1/085* (2013.01); *H01J 35/02* (2013.01); *H04N 5/321* (2013.01); *A61B 6/4035* (2013.01)

(56) References Cited

U.S. PATENT DOCUMENTS

| | | | |
|---|---|---|---|
| 6,064,715 A | 5/2000 | Sklebitz | |
| 6,543,936 B2 | 4/2003 | Feldman | |
| 7,289,602 B1 | 10/2007 | Polichar | |
| 8,023,722 B1 | 9/2011 | Kovarik | |
| 8,116,429 B2 * | 2/2012 | Bowers | A61B 5/4312 378/63 |
| 9,883,840 B2 | 2/2018 | Barbato | |
| 2008/0020332 A1 | 1/2008 | Lavenda | |
| 2009/0016490 A1 | 1/2009 | Campbell | |
| 2012/0033788 A1 | 2/2012 | Kovarik | |
| 2012/0148031 A1 | 6/2012 | Eaves | |
| 2013/0003923 A1 | 1/2013 | Sackett | |
| 2013/0195248 A1 | 8/2013 | Rothschild | |
| 2016/0174915 A1 * | 6/2016 | O'Dea | A61B 6/467 378/198 |
| 2017/0245827 A1 | 8/2017 | Joshi | |
| 2018/0153487 A1 * | 6/2018 | Eaves | A61B 6/4441 |
| 2020/0054294 A1 | 2/2020 | Belson | |

FOREIGN PATENT DOCUMENTS

| | | |
|---|---|---|
| WO | 2005081956 A3 | 9/2005 |
| WO | 2014022217 | 2/2014 |
| WO | 2016172611 | 10/2016 |

OTHER PUBLICATIONS

CMOSXRAY: "OpenVision LT Video RevA", YouTube, Jan. 20, 2011, p. 1, XP054979294, Retrieved from the Internet: URL:https://www.youtube.com/watch?v=ovU517D4zIM [retrieved on Apr. 10, 2019].

EOD Training with Vidisco, The Slovakian EOD Training School Plays it Safe with Vidisco, An interview with a Commander at the Slovakian EOD School by Rachel Lieberman.

GO-SCAN Portable Digital X-Ray Solution for NDT, Teledyne ICM.

Int'l Search Report and Written Opinion Appln. No. PCT/US2019/017041 dated May 7, 2019.

Int'l Search Report and Written Opinion Appln. No. PCT/US2019/017047 dated May 7, 2019.

Int'l Search Report and Written Opinion Appln. No. PCT/US2019/017051 dated May 7, 2019.

Int'l Search Report and Written Opinion Appln. No. PCT/US2019/017053 dated May 13, 2019.

MXR—Modular X-ray Robotic Scanner, © 2008-2016 Smart Imaging Systems Inc.

Portable X-Ray Generators, CP120B & CP160B, Constant potential ultralightweight battery powered X-ray generators for NDT and Security inspections, www.icmxray.com/ndt.

X-ray Sources, 60kV & 70kV 12W MAGPRO® Data Sheet, Tub-Data-1018, Rev B, Copyright © 2016, Moxtek.

Xplus SecurityRobot, Copyright 2015 Visiconsult GmbH.

The LIXI Profiler for Pipe Inspection https://lixi.com/lixi-profiler/ (archived Oct. 28, 2016).

* cited by examiner

SYSTEMS AND METHODS FOR DIGITAL X-RAY IMAGING

RELATED APPLICATIONS

This patent claims priority to U.S. Provisional Patent Application Ser. No. 62/627,473, filed Feb. 7, 2018, entitled "X-Ray Detectors for Generating Digital Images," U.S. Provisional Patent Application Ser. No. 62/627,469, filed Feb. 7, 2018, entitled "Systems and Methods for Digital X-Ray Imaging," U.S. Provisional Patent Application Ser. No. 62/627,464, filed Feb. 7, 2018, entitled "Systems and Methods for Digital X-Ray Imaging," and U.S. Provisional Patent Application Ser. No. 62/627,466, filed Feb. 7, 2018, entitled "Radiography Backscatter Shields and X-Ray Imaging Systems Including Backscatter Shields." The entireties of U.S. Provisional Patent Application Ser. No. 62/627,473, U.S. Provisional Patent Application Ser. No. 62/627,469, U.S. Provisional Patent Application Ser. No. 62/627,464, and U.S. Provisional Patent Application Ser. No. 62/627,466 are incorporated herein by reference.

BACKGROUND

This disclosure relates generally to radiography and, more particularly, to systems and methods for digital X-ray imaging.

SUMMARY

Systems and methods for digital X-ray imaging are disclosed, substantially as illustrated by and described in connection with at least one of the figures, as set forth more completely in the claims.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

The figures are not necessarily to scale. Wherever appropriate, similar or identical reference numerals are used to refer to similar or identical components.

DETAILED DESCRIPTION

Disclosed example handheld X-ray imaging systems enable real-time generation and/or display of digital images during X-ray radiography. In contrast with conventional systems, disclosed examples provide an all-in-one X-ray radiography unit that does not require extraneous equipment for power, X-ray generation, radiograph capture, radiograph display, or radiograph storage.

Disclosed example handheld X-ray imaging systems reduce operator fatigue relative to conventional scanning devices by having a reduced weight (e.g., less than 20 pounds) and/or by providing improved weight distribution that concentrates the weight of the handheld X-ray imaging system near the operator's body.

As used herein, the term "real-time" refers to the actual time elapsed in the performance of a computation by a computing device, the result of the computation being required for the continuation of a physical process (i.e., no significant delays are introduced). For example, real-time display of captured images includes processing captured image data and displaying the resulting output images to create the perception to a user that the images are displayed immediately upon capture. As used herein, the term "portable" includes handheld (e.g., capable of being carried and operated by a single person) and/or wheeled (e.g., capable of being transported and operated while wheels are attached and/or placed on wheels).

Figure 1:
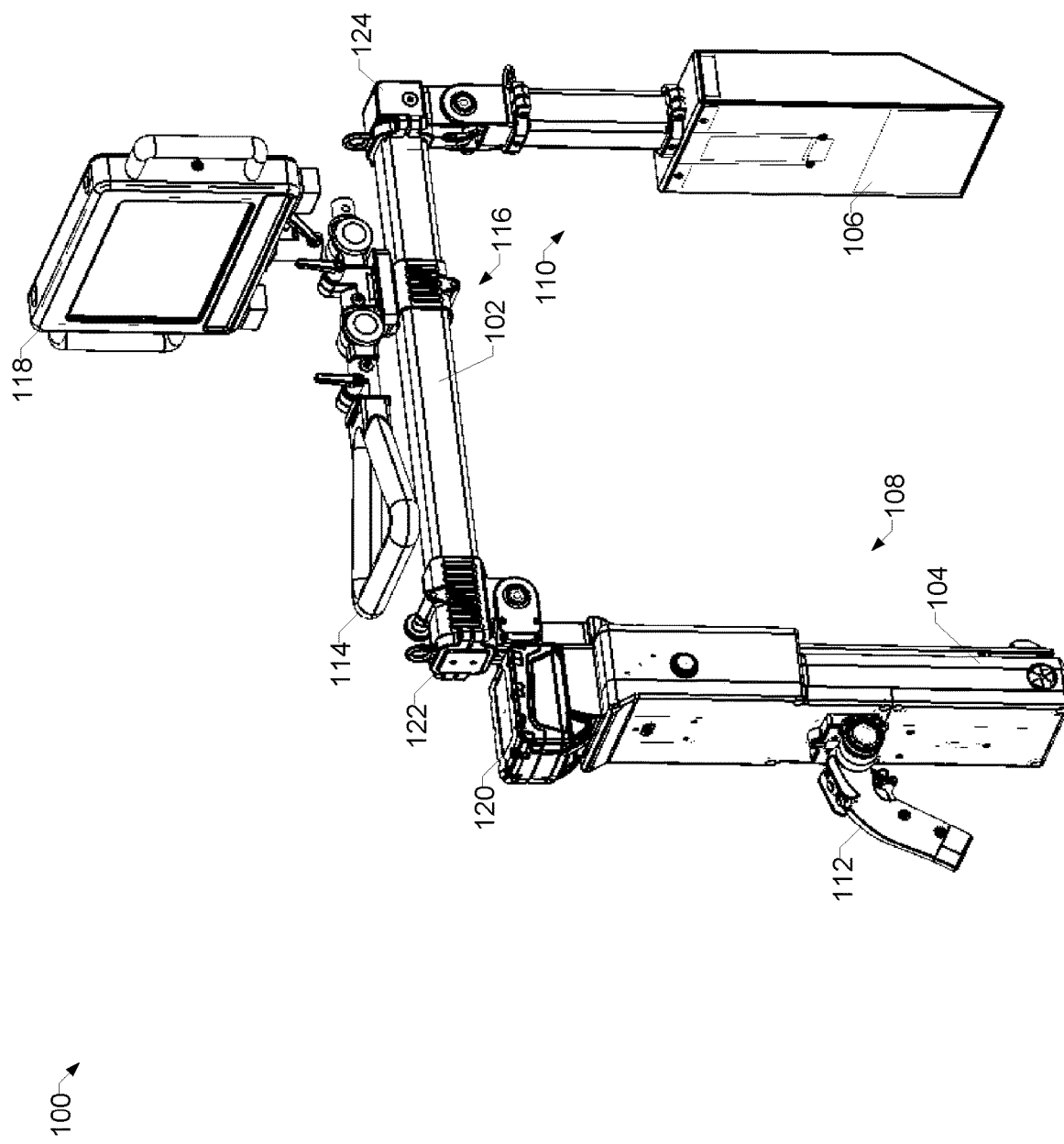
FIG. 1 is a perspective view of an example handheld X-ray imaging system to generate and output digital images and/or video based on incident X-rays, in accordance with aspects of this disclosure.

FIG. 1 is a perspective view of an example handheld X-ray imaging system 100 to generate and output digital images and/or video based on incident X-rays. The example handheld X-ray imaging system 100 may be used to perform non-destructive testing (NDT), medical scanning, security scanning, and/or any other scanning application.

The system 100 of FIG. 1 includes a frame 102 that holds an X-ray generator 104 and an X-ray detector 106. In the example of FIG. 1, the frame 102 is C-shaped, such that the X-ray generator 104 directs X-ray radiation toward the X-ray detector 106. As described in more detail below, the frame 102 is positionable (e.g., held by an operator, supported by an external support structure and/or manipulated by the operator, etc.) around an object to be scanned with X-rays. The example frame 102 is constructed using carbon fiber and/or machined aluminum.

The X-ray generator 104 is located on a first section 108 of the C-shaped frame 102 generates and outputs X-ray radiation, which traverses and/or scatters based on the state of the object under test. The X-ray detector 106 is located on a second section 110 of the frame 102 (e.g., opposite the first section 108) and receives incident radiation generated by the X-ray generator 104.

The example frame 102 may be manipulated using one or more handles 112, 114. A first one of the handles 112 is an operator control handle, and enables an operator to both mechanically manipulate the frame 102 and control the operation of the handheld X-ray imaging system 100. A second one of the handles 114 is adjustable and may be secured to provide the operator with leverage to manipulate the frame 102. The example handle 114 may be oriented with multiple degrees of freedom and/or adjusted along a length of a central section 116 of the frame 102.

During operation, the handheld X-ray imaging system 100 generates digital images (e.g., digital video and/or digital still images) from the X-ray radiation. The handheld X-ray imaging system 100 may store the digital images on one or more storage devices, display the digital images on a display device 118, and/or transmit the digital images to a remote receiver. The example display device 118 is attachable to the example frame 102 and/or may be oriented for viewing by the operator. The display device 118 may also be detached from the frame 102. When detached, the display device 118 receives the digital images (e.g., still images and/or video) via a wireless data connection. When attached, the display device 118 may receive the digital images via a wired connection and/or a wireless connection.

A power supply 120, such as a detachable battery, is attached to the frame 102 and provides power to the X-ray generator 104, the X-ray detector 106, and/or other circuitry of the handheld X-ray imaging system 100. An example power supply 120 that may be used is a lithium-ion battery pack. The display device 118 may receive power from the power supply 120 and/or from another power source such as an internal battery of the display device 118.

The example central section 116 of the frame 102 is coupled to the first section 108 via a joint 122 and to the second section 110 via a joint 124. The example joints 122, 124 are hollow to facilitate routing of cabling between the sections 108, 110, 116. The joints 122, 124 enable the first section 108 and the second section 110 to be folded toward the center section to further improve the compactness of the handheld X-ray imaging system 100 when not in use (e.g., during storage and/or travel).

Figure 2:
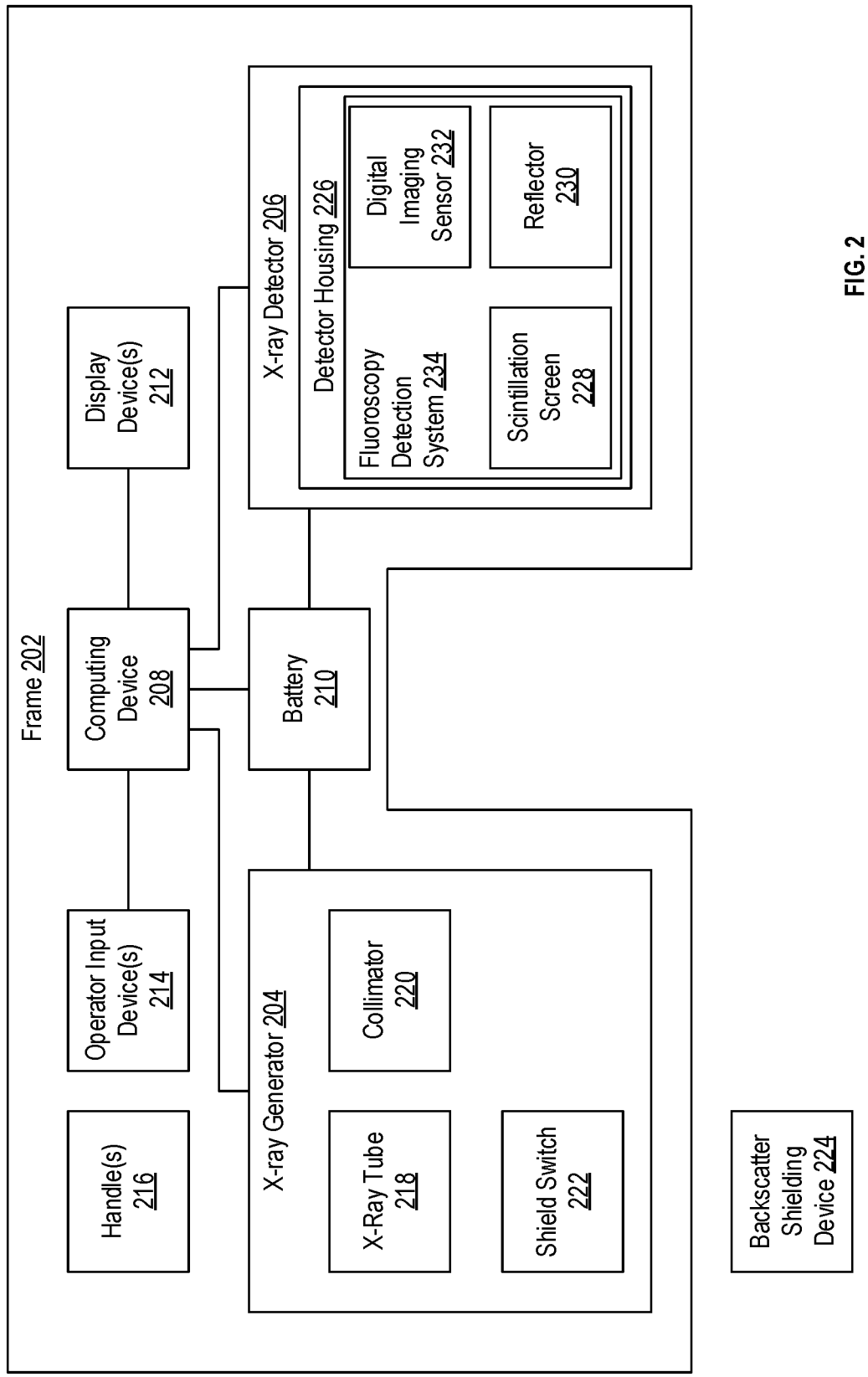
FIG. 2 is a block diagram of the example handheld X-ray imaging system of FIG. 1.

FIG. 2 is a block diagram of an example digital X-ray imaging system 200 that may be used to implement the handheld X-ray imaging system 100 of FIG. 1. The example digital X-ray imaging system 200 of FIG. 2 includes a frame 202 holding an X-ray generator 204, an X-ray detector 206, a computing device 208, a battery 210, one or more display device(s) 212, one or more operator input device(s) 214, and one or more handle(s) 216.

The X-ray generator 204 includes an X-ray tube 218, a collimator 220, and a shield switch 222. The X-ray tube 218 generates X-rays when energized. In some examples, the X-ray tube 218 operates at voltages between 40 kV and 120 kV. In combination with a shielding device, X-ray tube voltages between 70 kV and 120 kV may be used while staying within acceptable X-ray dosage limits for the operator. Other voltage ranges may also be used.

The collimator 220 filters the X-ray radiation output by the X-ray tube 218 to more narrowly direct the X-ray radiation at the X-ray detector 206 and any intervening objects. The collimator 220 reduces the X-ray dose to the operator of the system 200, reduces undesired X-ray energies to the detector 206 resulting from X-ray scattering, and/or improves the resulting digital image generated at the X-ray detector 206.

The shield switch 222 selectively enables and/or disables the X-ray tube 218 based on whether a backscatter shielding device 224 is attached to the frame. The backscatter shielding device 224 reduces the dose to the operator holding the frame 202 by providing shielding between the collimator 220 and an object under test. The example backscatter shielding device 224 includes a switch trigger configured to trigger the shield switch 222 when properly installed. For example, the shield switch 222 may be a reed switch or similar magnetically-triggered switch, and the backscatter shielding device 224 includes a magnet. The reed switch and magnet are respectively positioned on the frame 202 and the backscatter shielding device 224 such that the magnet triggers the reed switch when the backscatter shielding device 224 is attached to the frame 202. The shield switch 222 may include any type of a capacitive sensor, an inductive sensor, a magnetic sensor, an optical sensor, and/or any other type of proximity sensor.

The shield switch 222 is configured to disable the X-ray tube 218 when the backscatter shielding device 224 is not installed. The shield switch 222 may be implemented using, for example, hardware circuitry and/or via software executed by the computing device 208. In some examples, the computing device 208 may selectively override the shield switch 222 to permit operation of the X-ray tube 218 when the backscatter shielding device 224 is not installed. The override may be controlled by an administrator or other authorized user.

The X-ray detector 206 of FIG. 2 generates digital images based on incident X-ray radiation (e.g., generated by the X-ray tube 218 and directed toward the X-ray detector 206 by the collimator 220). The example X-ray detector 206 includes a detector housing 226, which holds a scintillation screen 228, a reflector 230, and a digital imaging sensor 232. The scintillation screen 228, the reflector 230, and the digital imaging sensor 232 are components of a fluoroscopy detection system 234. The example fluoroscopy detection system 234 is configured so that the digital imaging sensor 232 (e.g., a camera, a sensor chip, etc.) receives the image indirectly via the scintillation screen 228 and the reflector 230. In other examples, the fluoroscopy detection system 234 includes a sensor panel (e.g., a CCD panel, a CMOS panel, etc.) configured to receive the X-rays directly, and to generate the digital images. An example implementation of the X-ray detector 206 is described below with reference to FIGS. 5-8.

In some other examples, the scintillation screen 228, may be replaced with a solid state panel that is coupled to the scintillation screen 228 and has pixels that correspond to portions of the scintillation screen 228. Example solid state panels may include CMOS X-ray panels and/or CCD X-ray panels.

The computing device 208 controls the X-ray tube 218, receives digital images from the X-ray detector 206 (e.g., from the digital imaging sensor 232), and outputs the digital images to the display device 212. Additionally or alternatively, the computing device 208 may store digital images to a storage device. The computing device 208 may output the digital images as digital video to aid in real-time non-destructive testing and/or store digital still images.

As mentioned above, the computing device 208 may provide the digital images to the display device(s) 212 via a wired connection or a wireless connection. To this end, the computing device 208 includes wireless communication circuitry. For example, the display device(s) 212 may be detachable from the frame 202 and held separately from the frame 202 while the computing device 208 wirelessly transmits the digital images to the display device(s) 212. The display device(s) 212 may include a smartphone, a tablet computer, a laptop computer, a wireless monitoring device, and/or any other type of display device equipped with wired and/or wireless communications circuitry to communicate with (e.g., receive digital images from) the computing device 208.

In some examples, the computing device 208 adds data to the digital images to assist in subsequent analysis of the digital images. Example data includes a timestamp, a date stamp, geographic data, or a scanner inclination. The example computing device 208 adds the data to the images by adding metadata to the digital image file(s) and/or by superimposing a visual representation of the data onto a portion of the digital images.

The operator input device(s) 214 enable the operator to configure and/or control the example digital X-ray imaging system 200. For example, the operator input device(s) 214 may provide input to the computing device 208, which controls operation and/or configures the settings of the digital X-ray imaging system 200. Example operator input device(s) 214 include a trigger (e.g., for controlling activation of the X-ray tube 218), buttons, switches, analog joysticks, thumbpads, trackballs, and/or any other type of user input device.

The handle(s) 216 are attached to the frame 202 and enable physical control and manipulation of the frame 202, the X-ray generator 204, and the X-ray detector 206. In some examples, one or more of the operator input device(s) 214 are implemented on the handle(s) 216 to enable a user to both physically manipulate and control operation of the digital X-ray imaging system 200.

Figure 3:
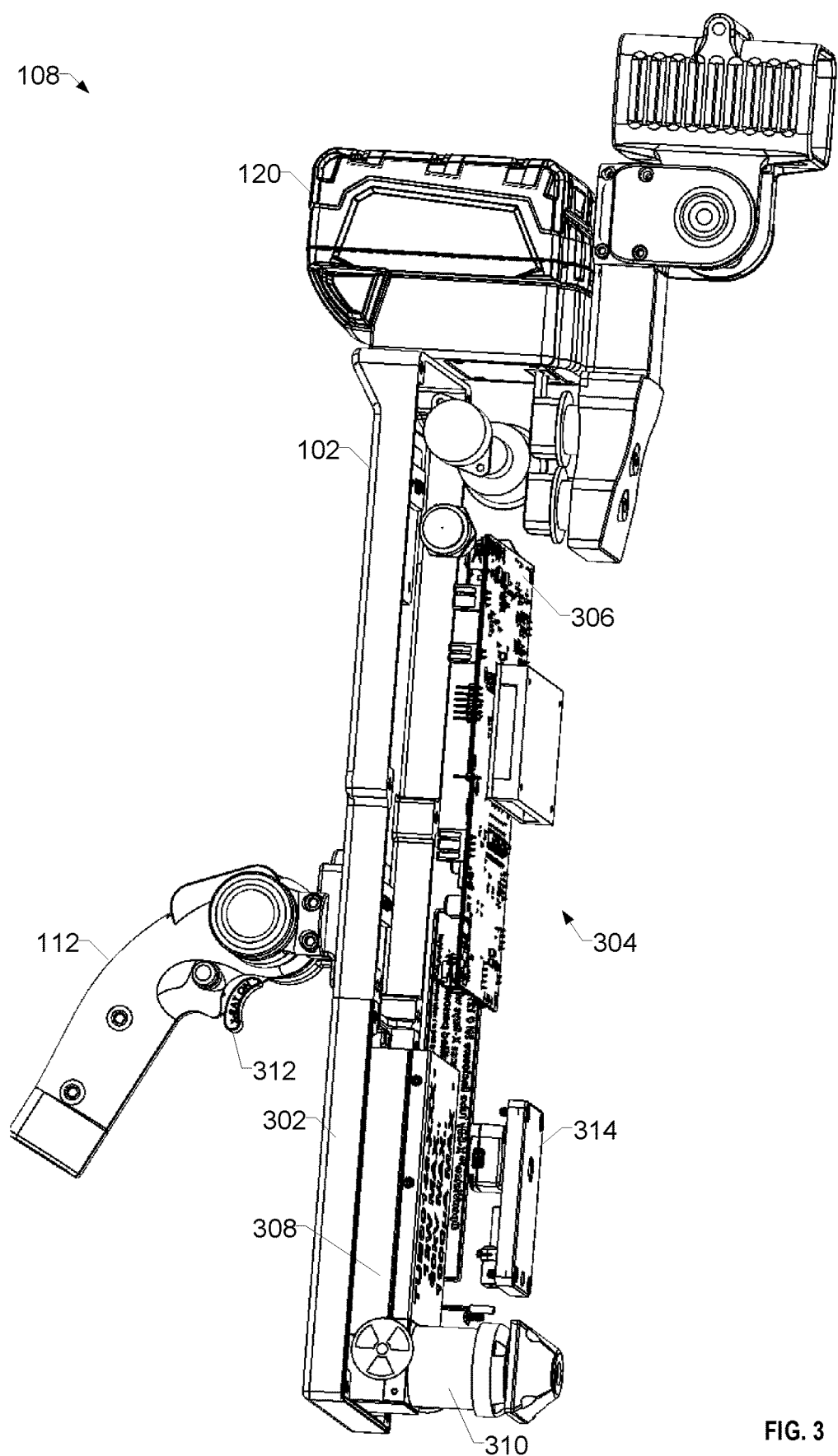
FIG. 3 is a perspective view of a first portion of the handheld X-ray imaging system of FIG. 1, including an X-ray generator, a power supply, an operator control handle.

FIG. 3 is a perspective view of the first portion 108 of the handheld X-ray imaging system 100 of FIG. 1, including the X-ray generator 104, the power supply 120, and the operator control handle 112. FIG. 3 is illustrated with a portion of a housing 302, while a second portion of the housing (shown in FIG. 1) is omitted for visibility of other components.

The example first portion 108 is further coupled to a computing device 304, such as the computing device 208 of FIG. 2. The computing device 304 is attached to the frame 102 via a printed circuit board 306.

An X-ray tube 308 (e.g., the X-ray tube 218 of FIG. 2) is coupled to a collimator 310 (e.g., the collimator 220 of FIG. 2) and controlled by the computing device 304 and/or by an operator input device on the handle 112. As shown in FIG. 3, the handle 112 may include an X-ray trigger 312 (e.g., one of the operator input device(s) 214 of FIG. 2). When actuated (e.g., by the operator of the handheld X-ray imaging system 100), the X-ray trigger 312 activates the X-ray tube 308 to generate X-ray radiation. The X-ray trigger 312 may activate the X-ray tube 308 directly and/or via the computing device 304.

The collimator 310 filters X-ray radiation generated by the X-ray tube 308 to reduce the X-ray radiation that is not directed at the X-ray detector 106 and/or to increase the proportion of X-ray radiation that is directed at the X-ray detector 106 (e.g., radiation that ends up being incident on a scintillator of the X-ray detector 106) relative to radiation not directed at the X-ray detector 106.

A targeting camera 314 is coupled to the computing device 304 to enable an operator of the handheld X-ray imaging system 100 to determine a target of generated X-rays. The example targeting camera 314 generates and outputs digital images (e.g., digital video, digital still images, etc.) to the computing device 304 for display to the operator via the display device 118. The digital images of the target (e.g., an exterior of the target) may be saved in association with the digital images of the X-ray scanning to provide contextual information about the location or object from which digital X-ray images are captured. Additionally or alternatively, a laser may be projected from the location of the targeting camera 314 toward the X-ray detector 106. The laser illuminates an approximate location on a workpiece that is being scanned by the digital X-ray imaging system 100 and/or output to the display device 118.

Figure 4:
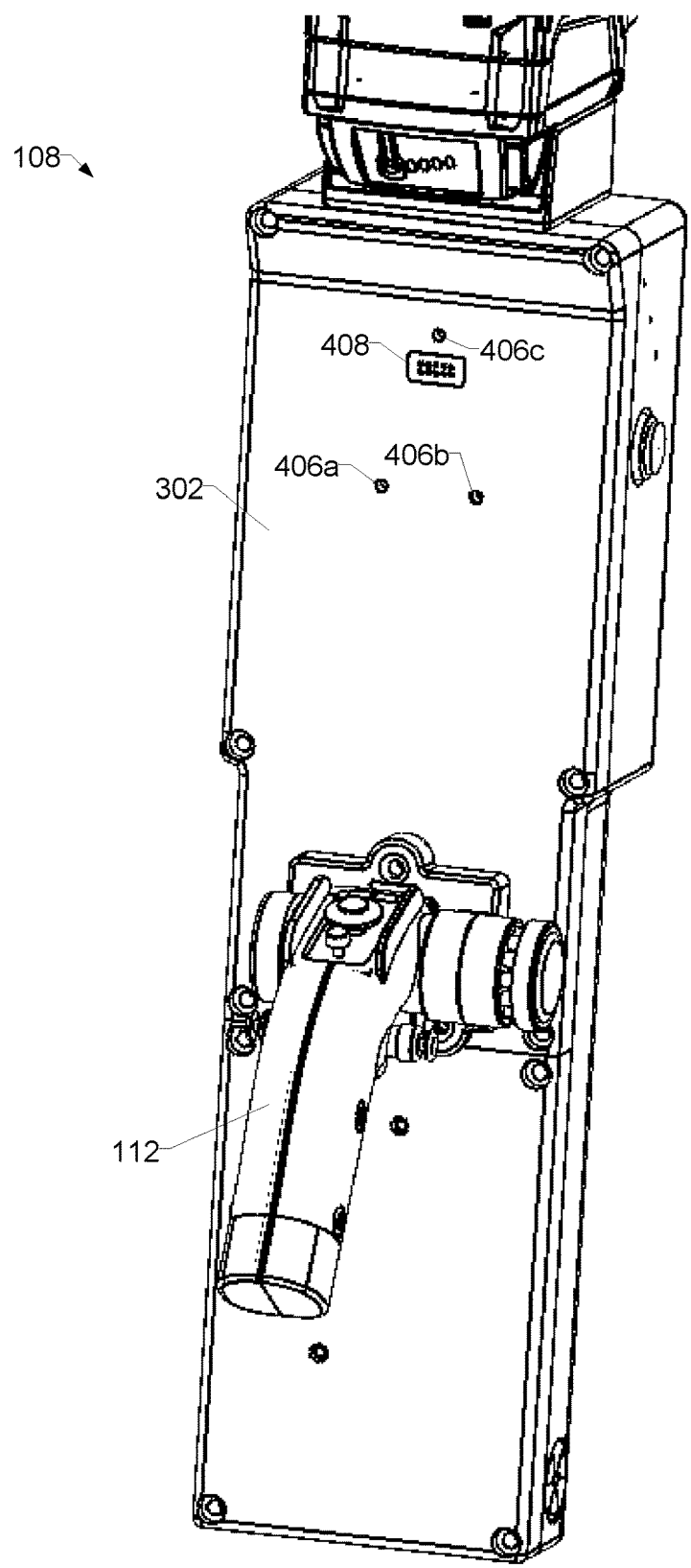
FIG. 4 is a more detailed view of the first portion of the handheld X-ray imaging system of FIG. 3 including the example handle.

FIG. 4 is a more detailed view of the first portion 108 of the handheld X-ray imaging system of FIG. 3 including the example handle 112. To improve the handling of the digital X-ray imaging system 100, the handle 112 is capable of attachment to multiple locations on the frame 102. The handle 112 is illustrated at a first location 402 on the frame 102 in FIG. 4. In the example of FIG. 4, the handle 112 is secured to the housing 302 via multiple screws.

The handle 112 may be detached from the first location 402 and attached at a second location 404. As illustrated in FIG. 4, the second location 404 on the housing 302 includes multiple screw nuts 406a-406c and a data connector 408, which match screw nuts and a data connector at the first location 402. The example handle 112 may be attached to the second location 404 by connecting a corresponding connector on the handle 112 to the data connector 408 and screwing the handle into the screw nuts 406a-406c.

Figure 5A:
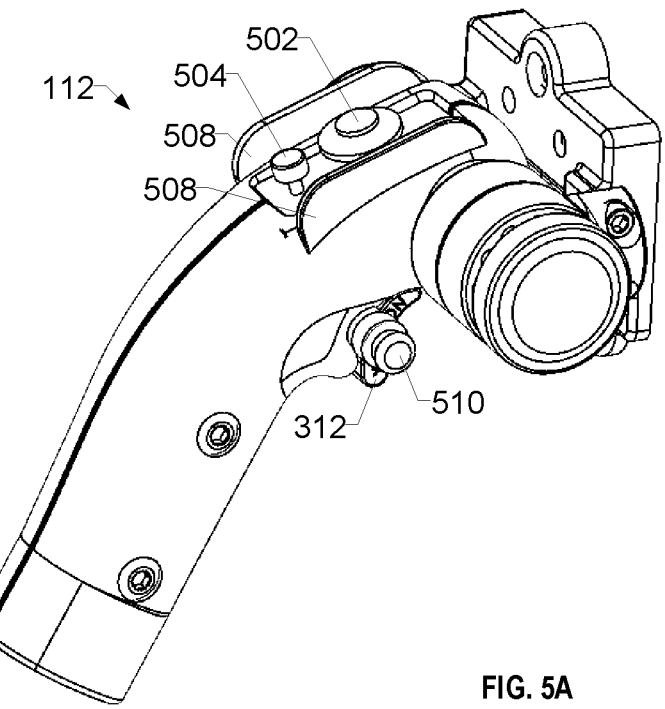
FIGS. 5A and 5B illustrate perspective views of the example handle of FIG. 3.
Figure 5B:
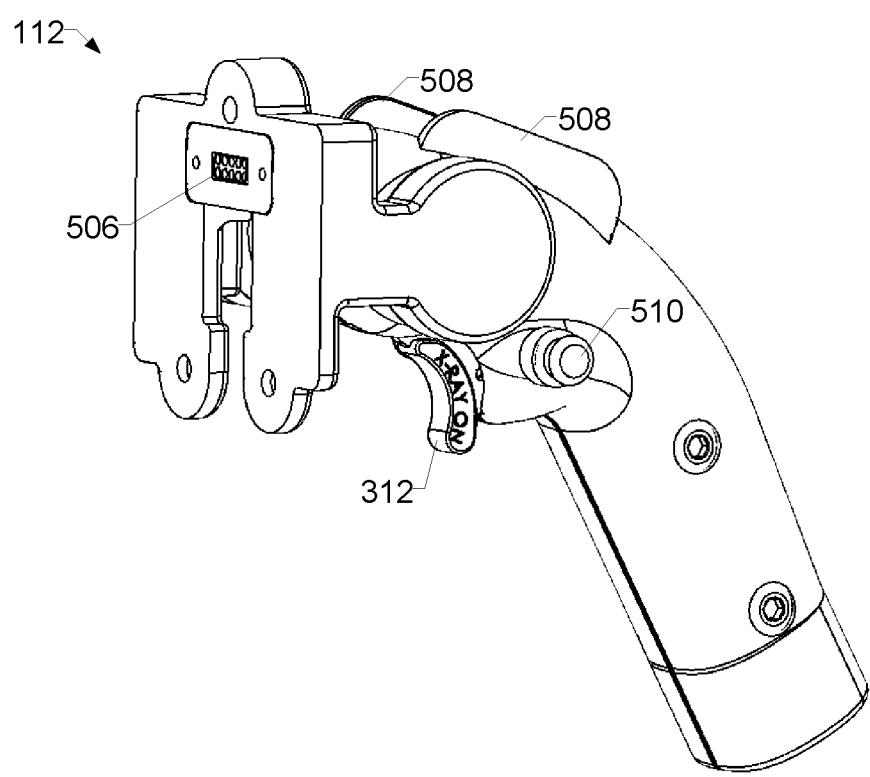

FIGS. 5A and 5B illustrate perspective views of the example handle 112 of FIGS. 1 and 3. As mentioned above, the handle 112 includes the trigger 312, which enables and/or activates the X-ray tube 308 to output the X-ray radiation. The handle 112 includes additional input devices 502, 504 (e.g., operator input devices 214 of FIG. 2). The input device 502 is a thumbstick, which can be used to input commands to the computing device 304, such as navigating menus, confirming selections, configuring the X-ray tube 308 and/or the X-ray generator 106, changing views and/or any other type of operator input. The input device 504 is a push button that may be used by an operator to confirm and/or cancel a selection. The computing device 304 controls the X-ray tube 308, the X-ray detector 106 (e.g., the X-ray generator 206 and/or the digital imaging sensor 232 of FIG. 2), the display device 118, and/or any other aspect of the digital X-ray imaging system 100 based on input from the trigger 312, the input devices 502, 504, and/or any other input devices.

The handle 112 includes a data connector 506, which mates to the data connector(s) 408 on the housing 302. The data connectors 408, 506 establish a hard-wired connection between the trigger 312 and/or the input devices 502, 504 and the computing device 304 and/or other circuitry.

The handle 112 includes input guards 508, which protect the input devices 502, 504 from accidental damage. The input guards 508 extend from the handle 112 adjacent the input devices 502, 504 and farther than the input devices 502, 504.

The example handle 112 further includes a trigger lock 510. The trigger lock 510 is a mechanical lock that, when activated, mechanically prevents activation of the trigger 312. The example trigger lock 510 is a push-button safety that locks the trigger 312 against depression by the operator.

Figure 6:
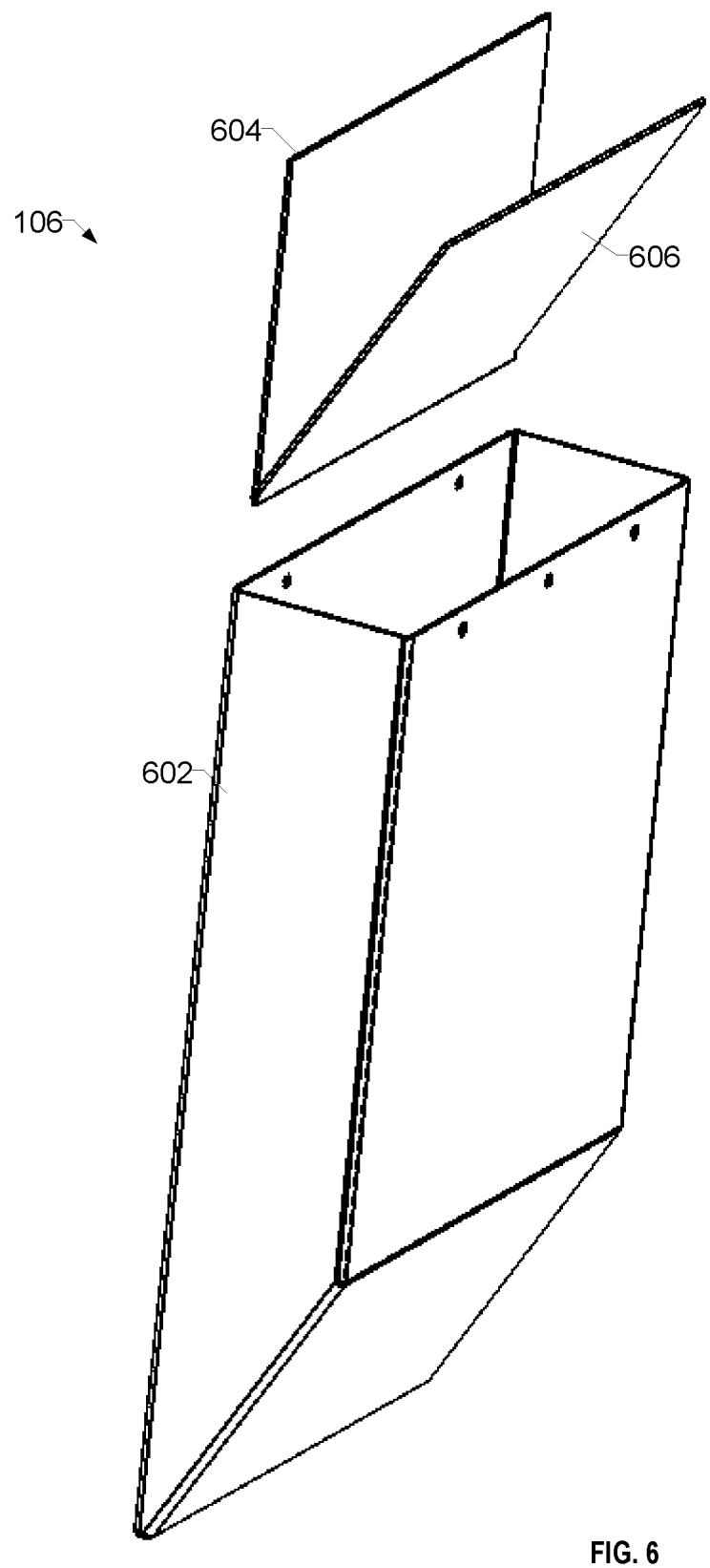
FIG. 6 is a partially exploded view of the example digital X-ray detector of FIG. 1.
Figure 7:
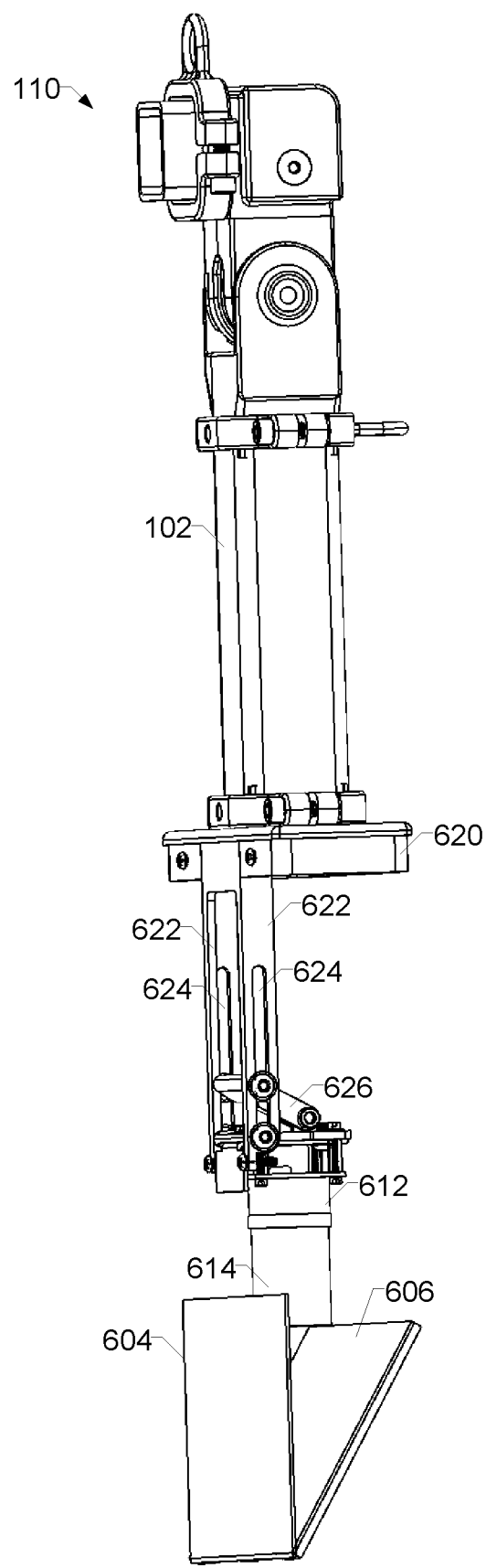
FIG. 7 is a perspective view of a first portion of the handheld X-ray imaging system of FIG. 1, including a digital X-ray detector assembly.

FIG. 6 is a partially exploded view of the example digital X-ray detector 106 of FIG. 1. FIG. 7 is a perspective view of the example digital X-ray detector 106 of FIG. 1. As illustrated in FIG. 6, the X-ray detector 106 includes a detector housing 602, a scintillation screen 604, and a reflector 606. The scintillation screen 604 and the reflector 606 are held within the housing 602 and are illustrated in FIG. 6 to show the relationship between the shape of the housing 602 and the geometries of the scintillation screen 604 and the reflector 606.

The detector housing 602 may be constructed using carbon fiber, aluminum, and/or any other material and/or combination of materials. The example detector housing 602 may function as a soft X-ray filter to reduce undesired X-ray radiation at the scintillation screen 604, thereby reducing noise in the resulting digital image. The scintillation screen 604 and/or the reflector 606 may be attached to the detector housing 602 using adhesive (e.g., epoxy, glue, etc.) and/or any other attachment technique. In some examples, the detector housing 602 is lined with a layer of lead or another backscatter shielding material to lower the dose to the operator in a handheld system.

Figure 8:
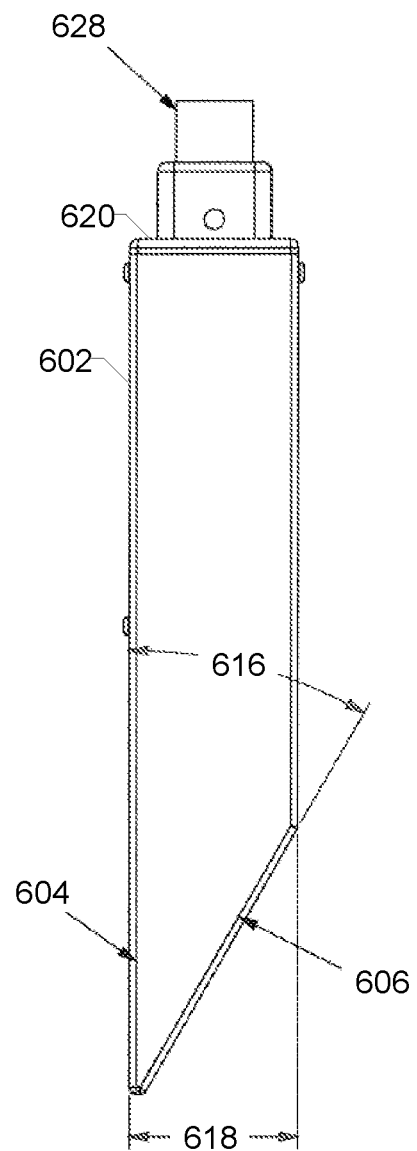
FIG. 8 is a side view of the example digital detector housing, the scintillator, and the reflector.
Figure 9:
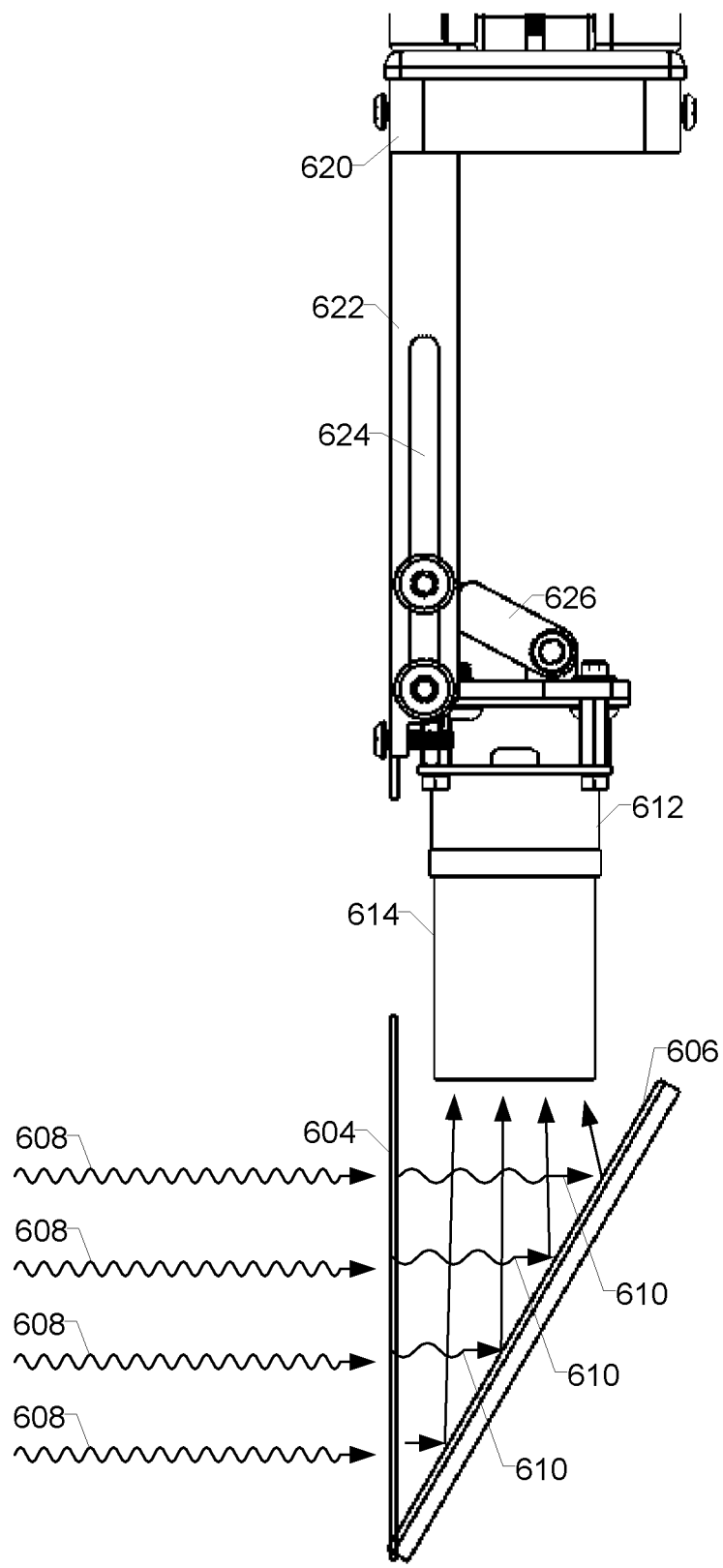
FIG. 9 is a side view of the example digital X-ray detector of FIG. 1, illustrating imaging of incident X-rays by the digital X-ray detector.

FIG. 8 is a side view of the example digital detector housing, the scintillator, and the reflector. FIG. 9 is a side view of the example digital X-ray detector 106 of FIG. 1, illustrating imaging of incident X-rays by the digital X-ray detector. As illustrated in FIG. 9, a digital imaging sensor 612 is oriented to capture light generated by the scintillation screen 604 in response to incident X-ray radiation.

The scintillation screen 604 converts incident X-rays 608 to visible light 610. An example scintillation screen 604 that may be used in a handheld X-ray scanner has a surface area of 4 inches by 6 inches. The size and material of the scintillation screen 604 at least partially determines the size, brightness, and/or resolution of the resulting digital images. The example scintillation screen is Gadox (Gadolinium oxysulphide) doped with Terbium, which emits a peak visible light at a wavelength of substantially 560 nm.

The example reflector 606 is a mirror that reflects visible light generated by the scintillation screen 604 to the digital imaging sensor 612 (e.g., via a lens 614). The example reflector 606 has the same surface area (e.g., 4 inches by 6 inches) as the scintillation screen 604, and is oriented at an angle 616 to direct the visible light 610 to the digital imaging sensor 612 and/or the lens 614. An example angle 616 is 30 degrees, which enables a 4 inch by 6 inch scintillation screen and a 4 inch by 6 inch reflector 606 to fit within a housing having a thickness 618 of less than 2.5 inches. In other examples, the angle 616 is an angle less than 45 degrees. Other sizes and/or geometries may be used for the scintillation screen 604 and/or the reflector 606. Additionally or alternatively, the digital X-ray detector 106 may include optics such as prisms to direct the visible light 610 to the digital imaging sensor 612.

The example digital imaging sensor 612 is a solid state sensor such as a CMOS camera. In the illustrated example using the scintillation screen 604 and the reflector 606, and a 6 mm lens 614, the digital imaging sensor 612 has a field of view of 143 degrees to capture light from substantially the entirety of the reflector 606.

The digital imaging sensor 612 is coupled to an imager bracket 620 via a mounting brackets 622. The detector housing 602 is also coupled to the imager bracket 620. The imager bracket 620 couples both the detector housing 602 and the digital imaging sensor 612 to the frame 102 of the handheld X-ray imaging system 100.

The mounting brackets 622 includes slots 624 to which an imaging bracket 626 is adjustably coupled. The digital imaging sensor 612 is attached to the imaging bracket 626 (e.g., via a printed circuit board). The imaging bracket 626 may be adjusted and secured along the length of the slots 624 to adjust an angle of the digital imaging sensor 612 relative to the reflector 606. The field of view of the digital imaging sensor 612 is oriented substantially perpendicularly to the scintillation screen, within the angular limits permitted using the slots 624 and the imaging bracket 626.

The example imager bracket 620 may include a data connector 628 (FIG. 8) to enable sufficient data throughput from the digital imaging sensor 612 to a computing device or other image display and/or image storage devices. An example data connector 628 may be a USB 3.0 connector to connect a USB 3.0 bus between the digital imaging sensor 612 and the receiving device. The USB 3.0 bus provides sufficient bandwidth between the digital imaging device 608 and the receiving device for high-definition video or better resolution.

While an example implementation of the X-ray detector 106 is described above, other example implementations of the X-ray detector 106 include using a solid state image sensor, such as a CMOS panel or a CCD panel, coupled directly to a scintillator. The CMOS panel produces digital images based on visible light generated by the scintillator, and outputs the digital images to the computing device 304.

Figure 10:
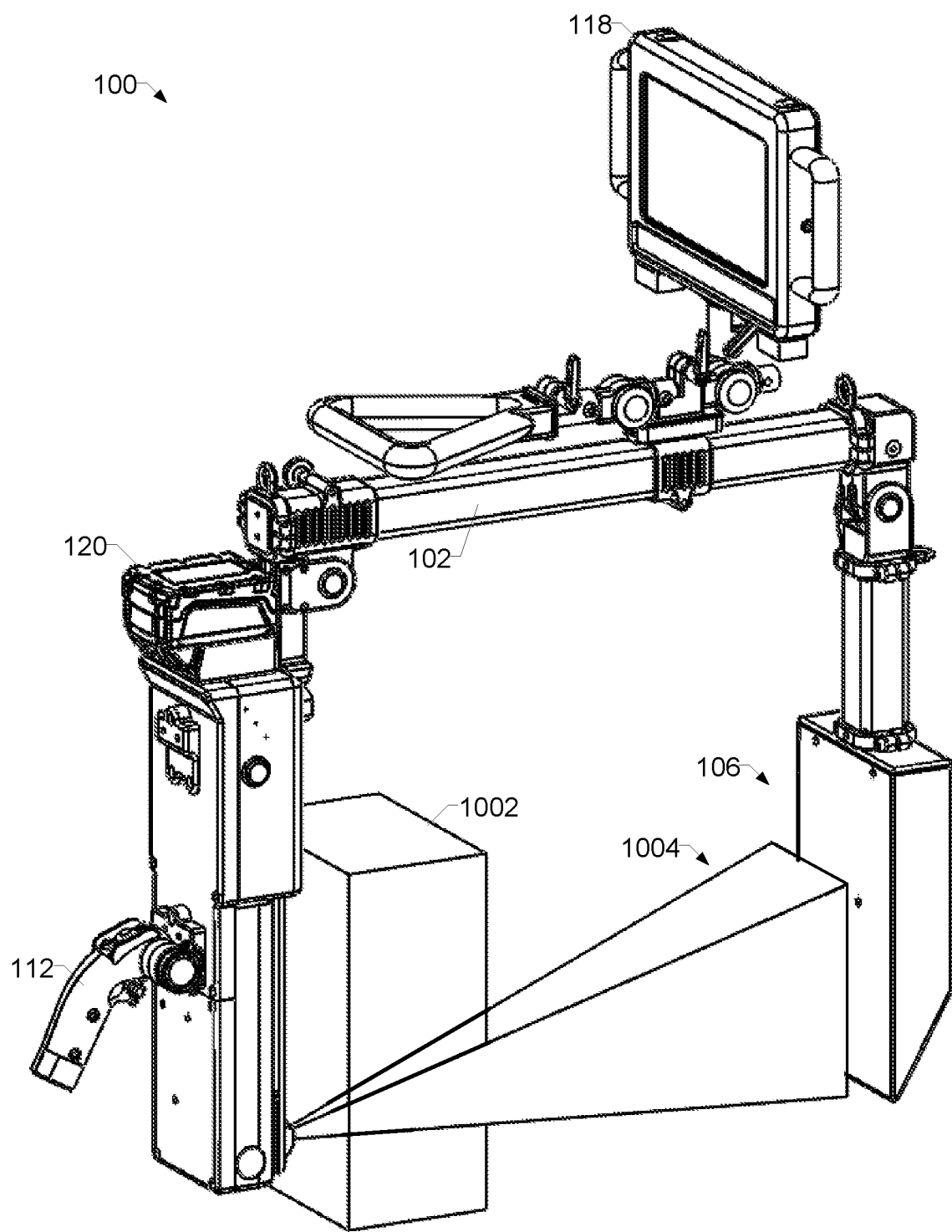
FIG. 10 is a side view of the handheld X-ray imaging system of FIG. 1, illustrating scanning of an object under test by directing X-rays from the X-ray tube to the X-ray detector.

FIG. 10 is a side view of the handheld X-ray imaging system of FIG. 1, illustrating scanning of an object 1002 under test by directing X-rays 1004 from the X-ray tube 308 to the X-ray detector 106. As mentioned above, the collimator 310 reduces X-ray radiation that is not directed at the X-ray detector 106, so the concentration of the X-ray radiation 1004 that is not scattered by the object 1002 is incident on the X-ray detector 106.

Figure 11:
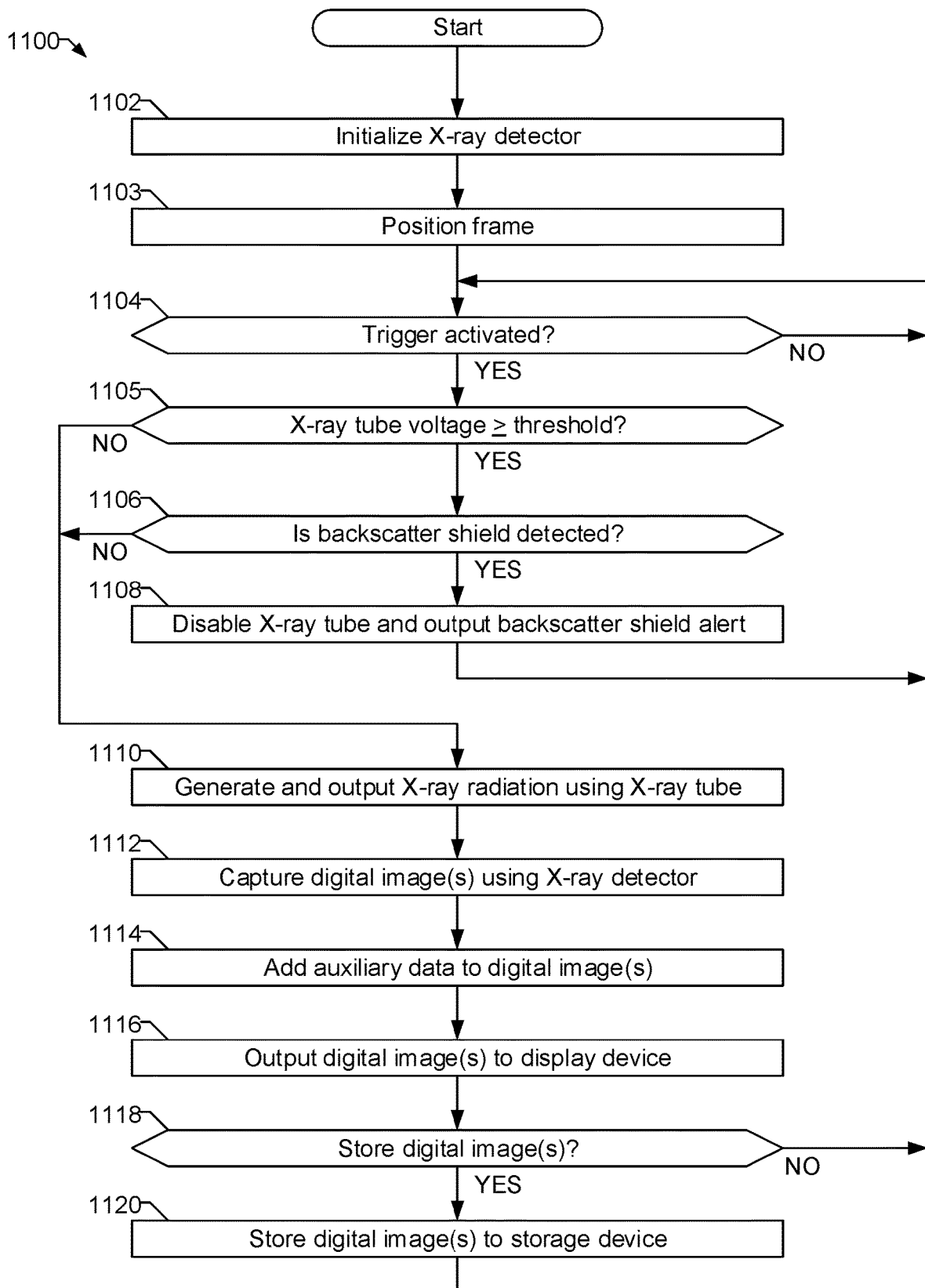
FIG. 11 is a flowchart representative of example machine readable instructions which may be executed by the example computing device of FIG. 2 to perform digital X-ray imaging, in accordance with aspects of this disclosure.

FIG. 11 is a flowchart representative of example machine readable instructions 1100 which may be executed by the example computing device 208 of FIG. 2 to perform digital X-ray imaging. The example machine readable instructions 1100 of FIG. 11 are described below with reference to the digital X-ray imaging system 200 of FIG. 2, but may be performed by the digital X-ray imaging system 100 of FIG. 1.

At block 1102, the example computing device 208 initializes the X-ray detector 206. For example, the computing device 208 may verify that the X-ray detector 206 is in communication with the computing device 208 and/or is configured to capture digital images of X-ray radiation. At block 1103, an operator of the digital X-ray imaging system 200 may position the frame 202 adjacent on object under test, such that the object under test is located between the X-ray detector 206 and the X-ray tube 218.

At block 1104, the computing device 208 determines whether a trigger is activated. For example, the computing device 208 may activate the X-ray tube 218 in response to activation of a trigger (e.g., a physical trigger, a button, a switch, etc.) by an operator. If the trigger has not been activated (block 1104), control returns to block 1104 to await activation of the trigger.

When the trigger is activated (block 1104), at block 1105 the computing device 208 determines whether the X-ray tube voltage is at least a threshold voltage. For example, the X-ray tube voltage may be configured to be between 70 kV and 120 kV, in which case the computing device 208 requires the backscatter shielding device 224 to be detected (e.g., via the shield switch 222).

If the X-ray tube voltage is at least the threshold (block 1105), at block 1106 the computing device 208 determines whether a backscatter shield is detected. For example, the computing device 208 may determine whether the backscatter shield (e.g., the backscatter shielding device 224, the backscatter shield 300, the backscatter shield 600) is installed using the shield switch 222. If the backscatter shield is not detected (block 1106), at block 1108 the computing device 208 disables the X-ray tube 218 and outputs a backscatter shield alert (e.g., via a visual and/or audible alarm, via the display device 212, etc.). Control then returns to block 1104.

If the backscatter shield is detected (block 1106), or if the X-ray tube voltage is less than the threshold (block 1105), at block 1110 the X-ray tube 218 generates and outputs X-ray radiation. At block 1112, the X-ray detector 106 (e.g., via the scintillation screen 228, the reflector 230, and the digital imaging sensor 232, and/or via a solid state panel coupled to a scintillator) captures digital image(s) (e.g., digital still images and/or digital video). The X-ray detector 106 provides the captured digital image(s) to the computing device 208. At block 1114, the computing device 208 adds the auxiliary data to the digital image(s). Example auxiliary data includes a timestamp, a date stamp, geographic data, and/or an inclination of the frame 202, the X-ray detector 206, the X-ray tube 218, and/or any other component of the digital X-ray imaging system 200. At block 1116, the computing device 208 outputs the digital image(s) to the display device(s) 218 (e.g., via a wired and/or wireless connection). In some examples, the computing device 208 outputs the digital image(s) to an external computing device such as a laptop, a smartphone, a server, a tablet computer, a personal computer, and/or any other type of external computing device.

At block 1118, the computing device 208 determines whether the digital image(s) are to be stored (e.g., in a storage device). If the digital image(s) are to be stored (block 1118), at block 1120 the example computing device 208 stores the image(s). The example computing device 208 may be configured to store the digital image(s) in one or more available storage devices, such as a removable storage device.

After storing the image(s) (block 1120), or if the digital image(s) are not to be stored (block 1118), control returns to block 1104. In some examples, blocks 1110-1120 may be iterated substantially continuously until the trigger is deactivated.

Figure 12:
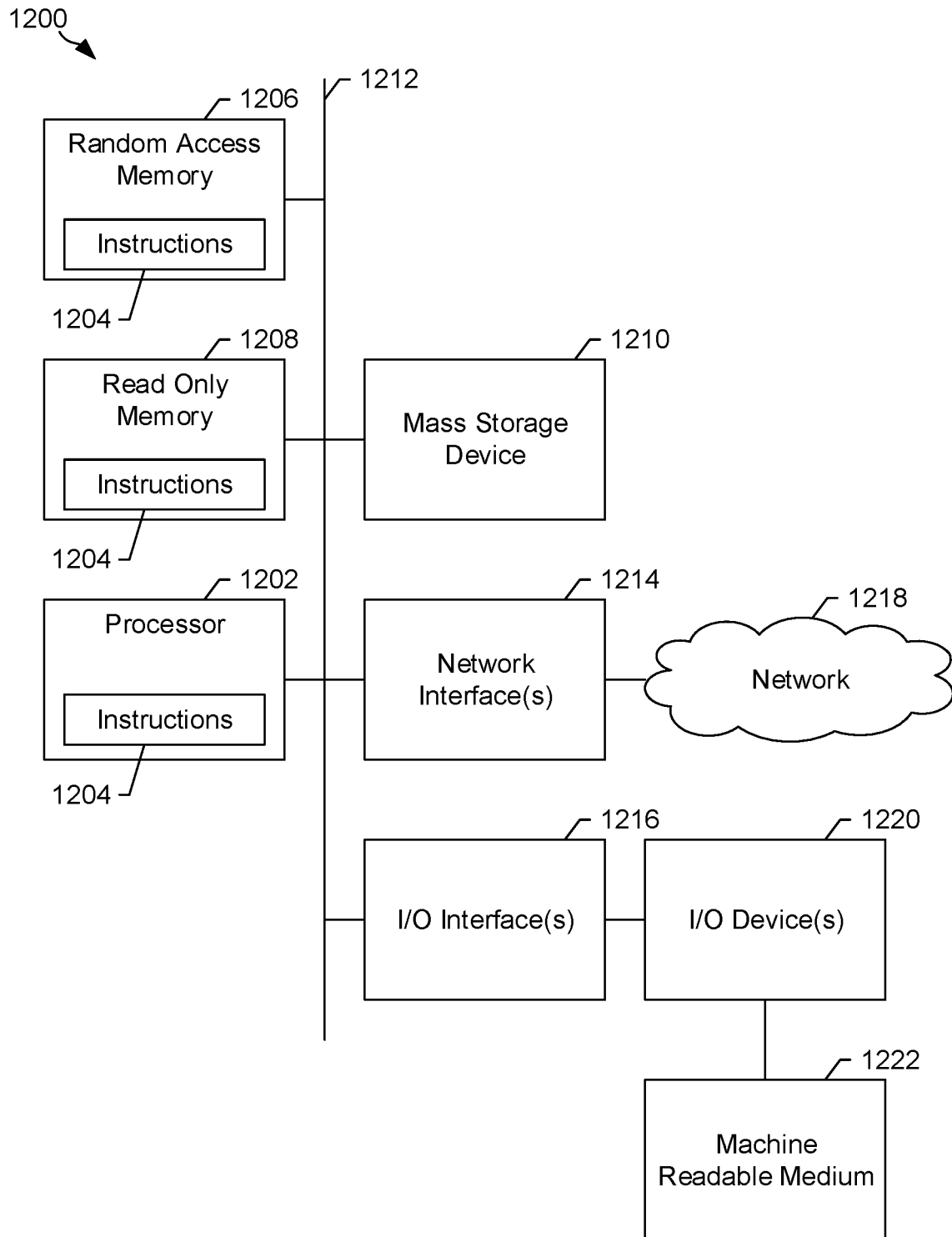
FIG. 12 is a block diagram of an example computing system that may be used to implement the computing device of FIG. 2.

FIG. 12 is a block diagram of an example computing system 1200 that may be used to implement the computing device 208 of FIG. 2. The example computing system 1200 may be implemented using a personal computer, a server, a smartphone, a laptop computer, a workstation, a tablet computer, and/or any other type of computing device.

The example computing system 1200 of FIG. 12 includes a processor 1202. The example processor 1202 may be any general purpose central processing unit (CPU) from any manufacturer. In some other examples, the processor 1202 may include one or more specialized processing units, such as RISC processors with an ARM core, graphic processing units, digital signal processors, and/or system-on-chips (SoC). The processor 1202 executes machine readable instructions 1204 that may be stored locally at the processor (e.g., in an included cache or SoC), in a random access memory 1206 (or other volatile memory), in a read only memory 1208 (or other non-volatile memory such as FLASH memory), and/or in a mass storage device 1210. The example mass storage device 1210 may be a hard drive, a solid state storage drive, a hybrid drive, a RAID array, and/or any other mass data storage device.

A bus 1212 enables communications between the processor 1202, the RAM 1206, the ROM 1208, the mass storage device 1210, a network interface 1214, and/or an input/output interface 1216.

The example network interface 1214 includes hardware, firmware, and/or software to connect the computing system 1200 to a communications network 1218 such as the Internet. For example, the network interface 1214 may include IEEE 1202.X-compliant wireless and/or wired communications hardware for transmitting and/or receiving communications.

The example I/O interface 1216 of FIG. 12 includes hardware, firmware, and/or software to connect one or more input/output devices 1220 to the processor 1202 for providing input to the processor 1202 and/or providing output from the processor 1202. For example, the I/O interface 1216 may include a graphics processing unit for interfacing with a display device, a universal serial bus port for interfacing with one or more USB-compliant devices, a FireWire, a field bus, and/or any other type of interface. Example I/O device(s) 1220 may include a keyboard, a keypad, a mouse, a trackball, a pointing device, a microphone, an audio speaker, an optical media drive, a multi-touch touch screen, a gesture recognition interface, a display device (e.g., the display device(s) 118, 212) a magnetic media drive, and/or any other type of input and/or output device.

The example computing system 1200 may access a non-transitory machine readable medium 1222 via the I/O interface 1216 and/or the I/O device(s) 1220. Examples of the machine readable medium 1222 of FIG. 12 include optical discs (e.g., compact discs (CDs), digital versatile/video discs (DVDs), Blu-ray discs, etc.), magnetic media (e.g., floppy disks), portable storage media (e.g., portable flash drives, secure digital (SD) cards, etc.), and/or any other type of removable and/or installed machine readable media.

Example wireless interfaces, protocols, and/or standards that may be supported and/or used by the network interface(s) 1214 and/or the I/O interface(s) 1216, such as to communicate with the display device(s) 212, include wireless personal area network (WPAN) protocols, such as Bluetooth (IEEE 802.15); near field communication (NFC) standards; wireless local area network (WLAN) protocols, such as WiFi (IEEE 802.11); cellular standards, such as 2G/2G+(e.g., GSM/GPRS/EDGE, and IS-95 or cdmaOne) and/or 2G/2G+(e.g., CDMA2000, UMTS, and HSPA); 4G standards, such as WiMAX (IEEE 802.16) and LTE; Ultra-Wideband (UWB); etc. Example wired interfaces, protocols, and/or standards that may be supported and/or used by the network interface(s) 1214 and/or the I/O interface(s) 1216, such as to communicate with the display device(s) 212, include comprise Ethernet (IEEE 802.3), Fiber Distributed Data Interface (FDDI), Integrated Services Digital Network (ISDN), cable television and/or internet (ATSC, DVB-C, DOCSIS), Universal Serial Bus (USB) based interfaces, etc.

The processor 202, the network interface(s) 1214, and/or the I/O interface(s) 1216, and/or the display device 212, may perform signal processing operations such as, for example, filtering, amplification, analog-to-digital conversion and/or digital-to-analog conversion, up-conversion/down-conversion of baseband signals, encoding/decoding, encryption/decryption, modulation/demodulation, and/or any other appropriate signal processing.

The computing device 208 and/or the display device 212 may use one or more antennas for wireless communications and/or one or more wired port(s) for wired communications. The antenna(s) may be any type of antenna (e.g., directional antennas, omnidirectional antennas, multi-input multi-output (MIMO) antennas, etc.) suited for the frequencies, power levels, diversity, and/or other parameters required for the wireless interfaces and/or protocols used to communicate. The port(s) may include any type of connectors suited for the communications over wired interfaces/protocols supported by the computing device 208 and/or the display device 212. For example, the port(s) may include an Ethernet over twisted pair port, a USB port, an HDMI port, a passive optical network (PON) port, and/or any other suitable port for interfacing with a wired or optical cable.

The present methods and systems may be realized in hardware, software, and/or a combination of hardware and software. The present methods and/or systems may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may include a general-purpose computing system with a program or other code that, when being loaded and executed, controls the computing system such that it carries out the methods described herein. Another typical implementation may comprise an application specific integrated circuit or chip. Some implementations may comprise a non-transitory machine-readable (e.g., computer readable) medium (e.g., FLASH drive, optical disk, magnetic storage disk, or the like) having stored thereon one or more lines of code executable by a machine, thereby causing the machine to perform processes as described herein. As used herein, the term "non-transitory machine-readable medium" is defined to include all types of machine readable storage media and to exclude propagating signals.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {. (x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

While the present method and/or system has been described with reference to certain implementations, it will be understood by those skilled in the art that various changes may be made and equivalents may be substituted without departing from the scope of the present method and/or system. For example, block and/or components of disclosed examples may be combined, divided, re-arranged, and/or otherwise modified. In addition, many modifications may be made to adapt a particular situation or material to the teachings of the present disclosure without departing from its scope. Therefore, the present method and/or system are not limited to the particular implementations disclosed. Instead, the present method and/or system will include all implementations falling within the scope of the appended claims, both literally and under the doctrine of equivalents.

The invention claimed is:

1. A portable X-ray scanner, comprising:
   an X-ray detector configured to generate digital images based on incident X-ray radiation;
   an X-ray tube configured to output X-ray radiation;
   a computing device configured to control the X-ray tube, receive the digital images from the X-ray detector, and output the digital images in real-time to a display device;
   a detachable battery configured to provide power to the X-ray tube, the X-ray detector, and the computing device;
   a frame configured to:
      hold the X-ray detector, the computing device, and the detachable battery; and
      hold the X-ray tube such that the X-ray tube directs the X-ray radiation to the X-ray detector; and
      enable a single user to position the X-ray detector and the X-ray tube while carrying the frame during output of the X-ray radiation; and
   a first handle configured to be movable along a center portion of the frame;
   wherein the portable X-ray scanner weighs less than 20 pounds.

2. The portable X-ray scanner of claim 1, further comprising:
   a second handle located on a side of the frame having the X-ray tube and having a trigger configured to enable a user to activate the X-ray tube to output the X-ray radiation.

3. The portable X-ray scanner of claim 2, wherein at least one of the first handle or the second handle is configured to be attachable to a plurality of locations on the frame.

4. The portable X-ray scanner of claim 2, wherein the second handle has a second input device, the computing device configured to control the X-ray tube or the digital imaging sensor based on an input received via the second input device.

5. The portable X-ray scanner of claim 1, wherein the computing device is configured to output the digital images to a data storage device.

6. The portable X-ray scanner of claim 1, wherein the computing device is configured to output digital video.

7. The portable X-ray scanner of claim 1, further comprising wireless communication circuitry, the computing device configured to output the digital images via the wireless communication circuitry.

8. The portable X-ray scanner of claim 1, wherein the X-ray detector comprises a fluoroscopy detection system comprising:
   a scintillator;
   a reflector; and
   a digital imaging sensor configured to generate the digital images from light generated by the scintillator and reflected by the reflector to the digital imaging sensor.

9. The portable X-ray scanner of claim 8, wherein the frame comprises a C-shaped frame, the X-ray scintillator and digital imaging sensor being on a first end of the C-shaped frame and the X-ray tube being on a second side of the C-shaped frame.

10. The portable X-ray scanner of claim 8, wherein the X-ray tube, the scintillator, and the digital imaging sensor are configured to generate the digital images using X-ray wavelengths for non-destructive testing of iron or aluminum materials.

11. The portable X-ray scanner of claim 8, further comprising a receiver housing configured to hold the X-ray scintillator and the digital imaging sensor, the receiving housing having a thickness of not more than 2.5 inches.

12. The portable X-ray scanner of claim 11, wherein the receiver housing is configured to hold an imager mirror configured to reflect light from the X-ray scintillator to the digital imaging sensor.

13. The portable X-ray scanner of claim 1, wherein the X-ray detector comprises a CCD panel, a CMOS panel, or a fluoroscopy detection system.

14. The portable X-ray scanner of claim 1, further comprising a collimator coupled to the X-ray tube and configured to filter the X-ray radiation.

15. The portable X-ray scanner of claim 1, wherein the computing device is configured to add to the digital images at least one of: a timestamp, a date stamp, geographic data, or a scanner inclination to the digital images.

16. The portable X-ray scanner of claim 1, further comprising the display device coupled to the frame.

17. The portable X-ray scanner of claim 1, wherein the frame comprises at least one of carbon fiber or machined aluminum.

18. The portable X-ray scanner of claim 1, wherein the portable X-ray scanner is configured to be handheld or portable via wheels.

* * * * *